United States Patent [19]

Maggi et al.

[11] 4,188,321
[45] * Feb. 12, 1980

[54] 25-DESACETYL RIFAMYCINS

[75] Inventors: Nicola Maggi; Piero Sensi, both of Milan, Italy

[73] Assignee: Gruppo Lepetit S.p.A., Milan, Italy

[*] Notice: The portion of the term of this patent subsequent to Mar. 24, 1989, has been disclaimed.

[21] Appl. No.: 679,195

[22] Filed: Oct. 30, 1967

[30] Foreign Application Priority Data

Nov. 3, 1966 [GB] United Kingdom ............... 49389/66

[51] Int. Cl.² ........................................... C07D 491/08
[52] U.S. Cl. ............................. 260/239.3 P; 424/244; 424/248.54; 424/250; 424/267; 424/274
[58] Field of Search ...................................... 260/239.3

[56] References Cited
U.S. PATENT DOCUMENTS

| | | | |
|---|---|---|---|
| 3,338,888 | 8/1967 | Bickel et al. | 260/239.3 |
| 3,342,810 | 9/1967 | Maggi et al. | 260/239.3 |
| 3,349,082 | 10/1967 | Maggi et al. | 260/239.3 |

OTHER PUBLICATIONS

Maggi et al., "Experientia" vol. 24, pp. 209–211 (1968).
Antimicrobial Agents and Chemotherapy—1966, edited by Gladys L. Hobby (1967), Title Page and Other Introductory pp. V and VI.
Bickel et al., II, "Antimicrobial Agents and Chemotherapy" 1967 red at a meeting of the American Society for Microbiology, Philadelphia, Pa., Oct. 26–28 (1966).
Fieser et al., "Organic Chemistry" 3rd Edition, p. 178 (Reinhold) (1956).

Primary Examiner—Alan L. Rotman
Assistant Examiner—Robert T. Bond
Attorney, Agent, or Firm—Ostrolenk, Faber, Gerb & Soffen

[57] ABSTRACT

The invention is concerned with a new class of rifamycins, namely, the 25-desacetylrifamycins, and with a process for their preparation. The new compounds display antibacterial activity quite similar to that shown by the parent 25-acetylrifamycins, and are characterized by a higher solubility and a lower toxicity than the parent substances.

4 Claims, No Drawings

25-DESACETYL RIFAMYCINS

The present invention relates to new antibiotic substances and to the process for their preparation.

In U.S. Pat. Spec. No. 3,150,046 the preparation of the antibiotic rifamycin by fermentation of a strain of Str. mediterranei ATCC 13685 is described. As stated in said patent rifamycin is a mixture of antibiotic substances.

One of these substances, rifamycin B, having the crude formula $C_{39}H_{49}NO_{14}$ is a diacid and one of the acidic groups is a carboxyl group. One of the particular properties of this antibiotic is an increase in activity when dissolved in water, i.e. to turn into another substance having higher antibacterial activity. The more active product, called rifamycin S, has the crude formula $C_{37}H_{45}NO_{12}$ and by mild reduction can be converted into another new antibiotic of the rifamycin class, rifamycin SV ($C_{37}H_{47}NO_{12}$). The process for preparing rifamycin SV comprises oxidation of rifamycin B to an intermediate rifamycin O; hydrolysis of rifamycin O to rifamycin S with release of glycolic acid and reduction of rifamycin S to rifamycin SV. Both rifamycin S and rifamycin SV lack the carboxyl group which is set free in the form of glycolic acid during the activation step.

The structure of rifamycins has been elucidated by Prelog and co-workers and published in Experientia 20, 336 (1964). Rifamycin B has the following structure:

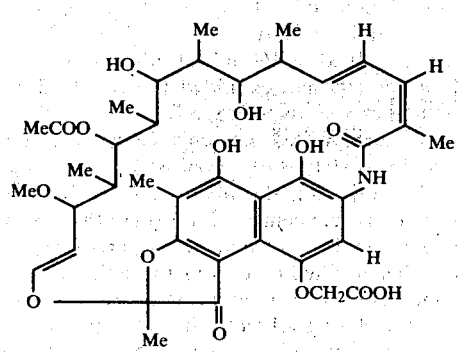

The above formula explains how rifamycin O, S and SV are produced from rifamycin B.

The sequence of such modifications may be illustrated by considering solely the naphthalene ring present in the molecule

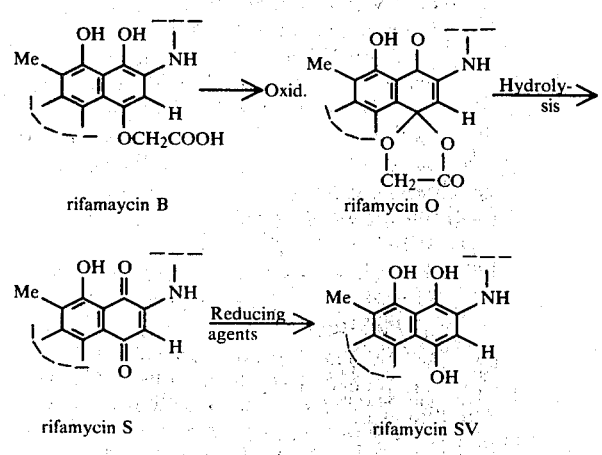

It is well known that many drugs, which possess a particular pharmacological activity in high degree, often find a limited medicinal use, owing to the fact that high blood or serum levels cannot be reached owing to the insolubility of said compounds in water and, therefore, in physiological liquids.

The aim of the present invention is to supply more soluble derivatives of the class of rifamycins. This is accomplished by hydrolysing the $CH_3COO$ group linked to $C_{25}$ so that a new hydroxy group is set free in the molecule. The process consists in treating the selected rifamycin derivative dissolved in a suitable solvent with an alkaline reagent, such as sodium bicarbonate, cyanide, hydroxide, organic bases etc.

The I.R. spectrum of the compounds obtained by the process, which may be called "25-desacetyl-rifamycins," is significantly different from the ones of the parent compounds because it shows a disappearing of the characteristic band of the acetyl group ($\nu=1710-1715$ cm$^{-1}$); the NMR spectrum confirms the disappearance of the methyl group of the acetyl group (which gives $\tau$ value from 7.93 to 8.02). Also the functional analysis confirms the disappearance of the acetyl group.

The whole class of rifamycins can be converted into 25-desacetyl-rifamycins according to the herein disclosed procedure, as it is apparent from the hereinafter appended Examples. For instance, the claimed process has been found to run with excellent results on rifamycins S and SV. Other rifamycins which are easily desacetylaceted are those bearing a substitution at position 3, such as 3-formylrifamycin SV, and its functional derivatives, i.e. those in which the 3-formyl group is bound with substances having a primary amino group forming a —CH:N—grouping, such as 3-(4-methylpiperazinyl-iminomethyl)-rifamycin SV, 3-methoximinomethyl-rifamycin SV, 3-phenylimino-methyl-rifamycin SV, the methyl-, ethyl-, propyl-, dimethyl-, diethyl-, dipropylhydrazone, and in general the mono- and dialkylhydrazones of 3-formylrifamycin SV, the oxime, the hydrazone, the arylhydrazone of 3-formylrifamycin SV, and many others. Other 3-substituted rifamycin have been found operative, such as the aminomethyl-derivatives (so-called Mannich bases), for instance the 3-amino-, 3-alkylamino and 3-dialkylaminomethylrifamycins S and SV, the analogues in which the basic moiety of the 3-substituent is a pyrrolidino, a piperidino, a morpholino, a piperazine radical, also substituted in the heterocyclic ring. Other rifamycins are those bearing a nitrogen-containing basic group at position 3, such as the 3-amino-, 3-pyrrolidino-, 3-morpholino-, 3-piperidino-, 3-piperazinorifamycins; or alternatively the amides and the hydrazides of rifamycin B, and the rifamycins having a condensed heterocyclic group at positions 3,4, such as the condensation products of rifamycin O and S with O-phenylenediamine, 2,3-diaminopyridine, 4,5-diamino-2-thiouracil, 2-aminophenol, 4-chloro- and 4-nitro-2-amino-phenol, 3-hydroxyanthranilic acid, I-amino-2naphthol, 3,4-diaminotoluene, and so on.

The obtained desacetyl-derivatives of the rifamycin S and SV, can be optionally converted into each other by means respectively of an appropriate reducing or oxidizing agent. Moreover, if a suitable hydrogenating agent is used, the corresponding hexahydro-derivatives in the aliphatic chain of the rifamycin molecule, can be obtained. These reactions are achieved according to well known methods. As an example the first two procedures can be carried out, using respectively ascorbic acid and potassium ferricyanide, while platinum dioxide can be used as the catalyst in the latter process.

The marked increase in solubility imparts very good antibacterial and antibiotic properties to the compounds and makes them particularly suitable for injectable use. The following table 1 summarizes comparatively the values of this essential physical property, relating to some compounds of the invention and to the corresponding 25-acetyl derivatives. Said solubilities are given in g. of rifamycin % ml. of buffer solution (pH=7,5 and t=22° C.). DA means desacetyl. It is apparent from this table that the 25-desacetyl rifamycins are much more soluble, and exactly from more than 2 and up to 50 times, in comparison with the corresponding 25-acetyl compounds.

TABLE 1

| Compound | Solubility g. % ml. (pH = 7,5; 22° C.) |
|---|---|
| 3-diethylaminomethyl-rifamycin SV | 0.042 |
| 25-DA-3-diethylaminomethyl-rifamycin SV | 0.126 |
| 3-pyrrolidino-methyl-rifamycin SV | 0.006 |
| 25-DA-3-pyrrolidino-methyl-rifamycin SV | 0.280 |
| 3-formyl-rifamycin SV | 0.640 |
| 25-DA-3-formyl-rifamycin SV | 3.43 |
| 3-methoximinomethyl-rifamycin SV | 0.015 |
| 25-DA-3-methoximinomethyl-rifamycin SV | 0.034 |
| 3-(4-methyl-piperazinyl-iminomethyl)-rifamycin SV | 0.285 |
| 25-DA-3-(4-methyl-piperazinyl-iminomethyl)-rifamycin SV | 0.760 |

An other advantage of the rifamycins forming the subject of the present application, is the surprisingly low toxicity, in comparison with that of the corresponding 25-acetyl compounds. This is apparent from table 2, where the values of the acute toxicity ($LD_{50}$) in mice, expressed in mg/kg, are given.

TABLE 2

| Compound | $LD_{50}$ mg/kg (mice) | |
|---|---|---|
| rifamycin B diethylamide | 340 | (i.v.) |
| 25-DA-rifamycin B diethylamide | 600 | (i.v.) |
| 3-formyl-rifamycin SV | 300 | (i.p.) |
| 25-DA-3-formyl-rifamycin SV | 550 | (i.p.) |
| 3-(4-methyl-piperazinyl-iminomethyl)-rifamycin SV | 460 | (i.p.) |
| 25-DA-3-(4-methyl-piperazinyl-iminomethyl)-rifamycin SV | 850 | (i.p.) |
| 3-methoximinomethyl-rifamycin SV | not absorbed | (i.p.) |
| 25-DA-3-(methoximinomethyl-rifamycin SV | 560 | (i.p.) |

The new 25-desacetylrifamycins are active against the same microorganisms as the parent rifamycins from which they are obtained according to the herein described processes, and are useful for the treatment of the same diseases. It is therefore apparent that as a rule the improved solubility and the lower toxicity permit administration of massive doses, decidedly superior to those employed with the corresponding non-desacetylated rifamycins, thus allowing prolonged treatment of stubborn cases. On the other hand, in many instances the increase in solubility is decisive for the preparation of parenterally administrable solutions. As a matter of fact, the extremely low solubility in water of the parent compounds would in many cases prevent the preparation of solutions of a sufficient concentration to be useful for parenteral administration.

The following non-limitative examples illustrate the invention.

EXAMPLE 1

Preparation of 25-desacetyl-3-diethylaminomethyl-rifamycin SV

To a solution of 7,8 g. (0.01 mole) of diethylaminomethyl-rifamycin SV (U.S. Pat. No. 3,349,082) dissolved in 160 ml. of ethanol, an aqueous 5% sodium bicarbonate is added (50 ml., 0.03 mole). The obtained mixture is refluxed for 8 hours, then it is cooled and concentrated in vacuo; 70 ml. of water are added and the mixture is extracted with 200 ml. of ethyl acetate after adjusting the pH at 4–4.5. The organic layer is dried and concentrated in vacuo; the desacetyl-derivative crystallizes out and, after separation by filtration, is further purified by chromatography on a silicagel column (275 g.), using an acetone-chloroform (1:3) mixture as the eluting solvent. The product obtained by concentration of the eluate weighs 5 g. (yield 68%). Decomposition point: 152°–158° C.

EXAMPLE 2

Preparation of 25-desacetyl-4-guanylazo-4-desoxy-rifamycin SV

An amount of 5 g. (0.0066 mole) of 4-guanylaxo-4-desoxy-rifamycin SV (the condensation product of rifamycin SV with aminoguanidine A. M. Greco et al., Il Farmaco, Ed.Sc. 16,755,765; P. Sensi, Research Progress in Organic Biological and Medicinal Chemistry. 1 (1964), 338–421) dissolved in 90 ml. of ethanol are treated with 34 ml. of aqueous 5% sodium bicarbonate (0.02 mole). The resulting solution is refluxed for 6 hours, then it is cooled and 250 ml. of water are added. The pH is adjusted to 2 with aqueous 10% hydrochloric acid, then an extraction is made with 300 ml. of ethyl acetate; the organic layer is cast off, because it contains some impurities together with a very limited portion of the end product. The aqueous layer is again extracted with ethyl acetate for 3 times, using totally 900 ml. of the organic solvent. The organic layers are brought together, they are repeatedly washed with a phosphate solution buffered at pH 7.5, until acetic acid present in the solution is entirely removed; then the solution is dried and concentrated in vacuo to small volume. The product crystallizes out, it is collected on a filter, washed with ethyl acetate and dried at 40° C.: it is analytically pure (yield 2.8 g.; 60%). Decomposition point: 228° C.

EXAMPLE 3

Preparation of 25-desacetyl-rifamycin S

An amount of 4.4 g. (0.0063 mole) of rifamycin S are dissolved at 15°-20° C. in 315 ml. of ethanolic 0.5% sodium hydroxide. The intense red-violet solution is stirred at room temperature for 3 hours, then it is poured into 1000 ml. of ice-water, and aqueous 10% hydrochloric acid is added up to acidic pH. The crude product crystallizes out and is extracted with ethyl acetate. The organic layer, washed with water and dried, is concentrated at reduced pressure to 100 ml.; 60 ml. of ligroin are added, then the solution is further concentrated to small volume; an amorphous yellow precipitate is formed, which is repeatedly crystallized from ethanol; the colour of the pure product is orange-yellow: 2.2 g. (54%) are obtained. Decomposition point: 144°-147° C.

EXAMPLES 4-8

EXAMPLE 9

Preparation of 25-desacetyl-rifamycin SV

A methanolic solution of desacetyl-rifamycin S is treated with an excess of aqueous sodium ascorbate solution and allowed to stand for a few minutes. The solution is then acidified, extracted with chloroform and the extract dried and evaporated. The residue consists of desacetyl-rifamycin SV having an $Rf_{RO}$ value of 0.52 (thin layer chromatogram on silica gel impregnated with citric acid, using chloroform with 10% methanol as running medium- the designation $Rf_{RO}$ meaning the Rf value as referred to that of rifamycin O as being equal to 1).

EXAMPLE 10

Preparation of 25-desacetyl-hexahydro-rifamycin S

Desacetyl rifamycin S obtained in known matter from rifamycin S is completely hydrogenated in ethanol using platinum dioxide as catalyst. 4 moles of hydrogen are taken up. The hydrogenation mixture is filtered, the filtrate evaporated, the residue dissolved in aqueous sodium bicarbonate solution, the solution oxidized by the addition of excess potassium ferricyanide solution,

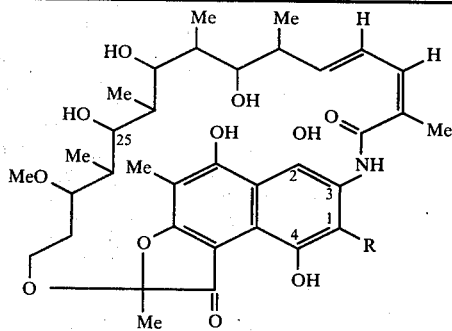

| Exam. | R | Empirical formula | Decomp. point | ΔRf(+) |
|---|---|---|---|---|
| 4 | —CH$_2$N—(CH$_2$)$_4$⌐ ⌙ | C$_{40}$H$_{54}$N$_2$O$_{11}$ | 178° C. | 0.19 (a) |
| 5 | —CHO | C$_{36}$H$_{45}$NO$_{12}$ | 161°-163° C. | 0.07 (b) |
| 6 | —CH=N—N⟨ ⟩N—Me | C$_{41}$H$_{56}$N$_4$O$_{11}$ | 165° C. | 0.15 (c) |
| 7 | —CH=N—C$_6$H$_5$ | C$_{42}$H$_{50}$N$_2$O$_{11}$ | 172° C. | 0.08 (b) |
| 8 | —CH=NOMe | C$_{37}$H$_{48}$N$_2$O$_{12}$ | 170°-230° C. | 0.12 (c) |

(+)The ΔRf value is the difference between the Rf value of the starting compound and the Rf value of the corresponding desacetyl derivative:
Rf$_{ac.}$ - Rf$_{desac.}$ Thin layer chromatography on silicagel G (Merck): run ∼ 10 cm.
Solvents mixtures:
(a) acetone-chloroform 1:1
(b) acetone-chloroform 2:1
(c) ethanol-chloroform 1:2

The preparation of the starting compound of Example 4 is disclosed in the above cited U.S. Pat. No. 2,349,082; while the preparation of those of Examples 5,6,7 and 8 and also of Example 16 hereinbelow, is disclosed in U.S. Pat. No. 3,342,810.

and the resulting desacetyl-hexahydro-rifamycin S extracted with chloroform. To remove resinous matter, the chloroformic solution is treated with some silica gel, then evaporated. The residue crystallizes slowly from aqueous methanol.

Melting point, 122°-130° C. Molecular weight, calculated: 659; found by mass spectrometry: 659.

EXAMPLE 11

Preparation of 25-desacetyl-hexahydro-rifamycin SV

A methanolic solution of desacetyl-hexahydro-rifamycin S, obtained according to Example 10 is treated with an excess of aqueous sodium ascorbate solution, and allowed to stand for a few minutes. The solution is then acidified and extracted with chloroform, and the extract dried and evaporated. The residue consists of desacetyl-hexahydro-rifamycin SV having an Rf$_{RO}$ value of 0.52 (thin layer chromatogram on silica gel impregnated with citric acid, using chloroform with 10% methanol as running agent—the designation Rf$_{RO}$ meaning the Rf value as referred to that of rifamycin O as being equal to 1).

EXAMPLE 12

Preparation of 25-desacetyl-3-methylamino-rifamycin S

A suspension of 2 g. of 3-methylamino-rifamycin S in 60 ml. of methanol is treated with 50 ml. of 10% sodium hydroxide solution and stirred for 10 minutes at room temperature. The solution is then acidified with citric acid, diluted with water, and extracted several times with chloroform. The chloroformic extracts are combined, dried and evaporated. The residue crystallizes from methanol+ether. 1.8 g. of wine-red prisms of desacetyl-3-methylamino-rifamycin S are obtained which melt at 208° C.

The starting compound of this example, as well as of Examples 13, 14, 15 and 17 hereinbelow, are obtained as described in Belgian Pat. No. 685,866.

EXAMPLE 13

Preparation of 25-desacetyl-3-methylamino-rifamycin SV

A methanolic solution of desacetyl-3-methylamino-rifamycin S is treated with an excess of aqueous sodium ascorbate solution and allowed to stand for a few minutes. The solution is then acidified, extracted with chloroform, and the residue dried and evaporated. The residue consists of desacetyl-3-methylamino-rifamycin SV which has an Rf$_{RO}$ value of 0.35 (thin layer chromatogram on silica gel impregnated with citric acid, using chloroform with 10% methanol as running agent—the designation Rf$_{RO}$ meaning the Rf value as referred to that of rifamycin O as being equal to 1).

EXAMPLE 14

Preparation of 25-desacetyl-3-morpholino-rifamycin SV 5.0 g. of 3-morpholino-rifamycin SV are dissolved in a large excess of 2N-sodium hydroxide solution, and the solution is allowed to stand at room temperature for 45 minutes. It is then neutralized, acidified with citric acid, and extracted several times with chloroform. The chloroformic extracts are combined, dried and evaporated. The residue is recrystallized twice from ether to yield 4.2 g. of desacetyl-3-morpholino-rifamycin SV in the form of long, yellow prisms melting at 240° C. (with decomposition).

EXAMPLE 15

Preparation of 25-desacetyl-3-morpholino-rifamycin S

An aqueous solution of the sodium salt of desacetyl-3-morpholino-rifamycin SV is treated with an excess of aqueous potassium ferricyanide solution. A red-brown precipitate forms and is extracted with chloroform. The chloroformic extract is dried and evaporated and the residue crystallized from ether. Red-violet crystals of the desacetyl-3-morpholino-rifamycin S are obtained which melt and decompose at 175°–178° C.

EXAMPLE 16

Preparation of 25-desacetyl-3-dimethylhydrazono-methyl-rifamycin SV.

5 g. of 3-dimethylhyrazono-methyl-rifamycin SV are suspended in 100 ml. of methanol, 50 ml. of 10% sodium hydroxide solution are added, followed by 100 ml. of methanol, and the whole is allowed to stand at room temperature for 40 minutes. The batch is then acidified with citric acid, diluted with water, and extracted several times with chloroform. The chloroformic extracts are combined, dried and evaporated. The residue which is formed by the desacetyl-3-dimethylhydrazono-methyl-rifamycin SV crystallizes from methanol.

Yield: 4.0 g.; melting point: 179°–181° C.

EXAMPLE 17

Preparation of 25-desacetyl-3-piperidino-rifamycin SV

A methanolic solution of 2.0 g. of 3-piperidino-rifamycin SV is treated with 5 ml. of 20% sodium hydroxide solution and allowed to stand at room temperature for 45 minutes. The solution is then acidified with citric acid, diluted with water, and extracted with chloroform. The chloroformic extract is dried and evaporated. The residue crystallizes from methanol in the form of yellow prisms. 1.5 g. of desacetyl-3-piperidino-rifamycin SV of melting point 242°–245° C. (decomposition) are obtained.

We claim:
1. 25-desacetyl-3-(4-methyl-piperizinyl-iminomethyl)-rifamycin SV.
2. 25-desacetyl-3-phenyl-iminomethyl-rifamycin SV.
3. 25-desacetyl-3-methoximinomethyl-rifamycin SV.
4. 25-desacetyl-3-dimethylhydrazono-methyl-rifamycin SV.

* * * * *